US010890513B2

(12) United States Patent
Mukaisho et al.

(10) Patent No.: US 10,890,513 B2
(45) Date of Patent: Jan. 12, 2021

(54) CELL-HOLDING SUBSTRATE HOLDER FOR PREPARING OBSERVATION SPECIMEN, KIT INCLUDING SAME, AND OBSERVATION SPECIMEN PREPARATION METHOD

(71) Applicants: NATIONAL UNIVERSITY CORPORATION SHIGA UNIVERSITY OF MEDICAL SCIENCE, Shiga (JP); JAPAN VILENE COMPANY, LTD., Tokyo (JP)

(72) Inventors: Ken-ichi Mukaisho, Shiga (JP); Takanori Hattori, Shiga (JP); Takuya Iwasa, Ibaraki (JP); Masaaki Kawabe, Ibaraki (JP); Satoshi Kumagai, Tokyo (JP)

(73) Assignees: NATIONAL UNIVERSITY CORPORATION SHIGA UNIVERSITY OF MEDICAL SCIENCE, Shiga (JP); JAPAN VILENE COMPANY, LTD., Tokyo (JP)

( * ) Notice: Subject to any disclaimer, the term of this patent is extended or adjusted under 35 U.S.C. 154(b) by 175 days.

(21) Appl. No.: 15/759,719

(22) PCT Filed: Sep. 14, 2016

(86) PCT No.: PCT/JP2016/077056
§ 371 (c)(1),
(2) Date: Mar. 13, 2018

(87) PCT Pub. No.: WO2017/047617
PCT Pub. Date: Mar. 23, 2017

(65) Prior Publication Data
US 2018/0340869 A1 Nov. 29, 2018

(30) Foreign Application Priority Data

Sep. 14, 2015 (JP) ................................. 2015-180832
Sep. 14, 2015 (JP) ................................. 2015-180833
Jun. 8, 2016 (JP) ................................. 2016-114067

(51) Int. Cl.
| | | |
|---|---|---|
| *G01N 1/31* | (2006.01) |
| *G01N 1/30* | (2006.01) |
| *G02B 21/34* | (2006.01) |
| *G01N 1/40* | (2006.01) |
| *G01N 33/483* | (2006.01) |
| *G01N 1/28* | (2006.01) |

(52) U.S. Cl.
CPC .............. *G01N 1/31* (2013.01); *G01N 1/30* (2013.01); *G01N 1/312* (2013.01); *G01N 1/4077* (2013.01); *G01N 33/4833* (2013.01); *G02B 21/34* (2013.01); *G01N 1/2813* (2013.01); *G01N 2001/4088* (2013.01)

(58) Field of Classification Search
CPC ............. G01N 2001/4088; G01N 1/31; G01N 33/4833; G02B 21/34
See application file for complete search history.

(56) References Cited

U.S. PATENT DOCUMENTS

| | | | |
|---|---|---|---|
| 3,615,257 | A | 10/1971 | Frost et al. |
| 5,484,572 | A | 1/1996 | Katakura et al. |
| 5,578,459 | A | 11/1996 | Gordon et al. |
| 6,436,662 | B1 | 8/2002 | Mielzynska et al. |
| 2003/0010894 | A1 | 1/2003 | Yoshihara et al. |
| 2004/0067482 | A1 | 4/2004 | Yasuda et al. |
| 2009/0226957 | A1 | 9/2009 | Paterlini-Brechot |
| 2013/0327722 | A1 | 12/2013 | Siddiqui et al. |
| 2015/0198508 | A1 | 7/2015 | Ebi et al. |
| 2016/0195458 | A1 | 7/2016 | Kikuhara et al. |

FOREIGN PATENT DOCUMENTS

| | | |
|---|---|---|
| CN | 202393969 U | 8/2012 |
| CN | 103484357 A | 1/2014 |
| EP | 0857961 A2 | 8/1998 |
| EP | 2902476 A1 | 8/2015 |
| JP | 62-121331 A | 6/1987 |
| JP | 62121331 A * | 6/1987 |
| JP | 04-001433 U1 | 1/1992 |
| JP | 04-165321 A | 6/1992 |

(Continued)

OTHER PUBLICATIONS

International Search Report (and English translation) and Written Opinion of the International Searching Authority for PCT/JP2016/077056, dated Dec. 13, 2016.

(Continued)

*Primary Examiner* — Heidi Reese
(74) *Attorney, Agent, or Firm* — Heslin Rothenberg Farley & Mesiti P.C.

(57) ABSTRACT

Provided are a cell-holding substrate holder for preparing an observation specimen, and a cell-holding substrate kit, wherein the cell-holding substrate can be easily attached and detached. Also provided is a method of preparing an observation specimen, wherein cell organelles can be satisfactorily observed using an optical microscope, while three problems of cell detachment, drying, and loss of the three-dimensional properties can be simultaneously solved. The cell-holding substrate holder comprises (1) a support plate 1 having a cell-holding substrate arrangement portion 12 having a window portion through which water can pass; and (2) a removable sandwiching plate 2, 3 which has a window portion through which water can pass, and is capable of working in conjunction with the support plate 1 to sandwich and fix a cell-holding substrate 9 in the cell-holding substrate arrangement portion 12. The cell-holding substrate kit 10 comprises the cell-holding substrate holder and a cell-holding substrate 9. In the preparation method, cells are collected with an inorganic fiber aggregate, wet-fixed as they are, stained, and mounted with a mounting medium having a refractive index equivalent to that of the inorganic fiber.

15 Claims, 6 Drawing Sheets

(56) References Cited

FOREIGN PATENT DOCUMENTS

| | | |
|---|---|---|
| JP | 09-505890 A | 6/1997 |
| JP | 11-507724 A | 7/1999 |
| JP | 2003-529768 A | 10/2003 |
| JP | 2004-298158 A | 10/2004 |
| JP | 2006-010437 A | 1/2006 |
| JP | 2008-537485 A | 9/2008 |
| JP | 200985838 A | 4/2009 |
| JP | 2010-185164 A | 8/2010 |
| JP | 2012-075383 A | 4/2012 |
| KR | 100476273 B1 | 3/2005 |
| WO | 96/41153 A1 | 12/1996 |
| WO | 2014/050963 A1 | 4/2014 |
| WO | 2015/019889 A1 | 2/2015 |

OTHER PUBLICATIONS

English Translation of the Written Opinion of the International Searching Authority for PCT/JP2016/077056 dated Dec. 13, 2016.

GE Healthcare Japan Corporation, Glass fiber filter paper, Japan, Jan. 16, 2010, [online], [Searched on Aug. 16, 2019], internet, <URL: https://www.gelifesciences.co.jp/catalog/1324.html> (with English Machine translation thereof obtained Aug. 17, 2020).

Kensa to Gijyutsu (Modern Medical Laboratory), Japan, Jun. 5, 2001, vol. 29, No. 7, p. 789, [online], [Searched on Aug. 16, 2019], internet, <URL:https://webview.isho.jp/journal/detail/abs/10.11477/mf.1543905892> (with English Machine translation thereof obtained Aug. 17, 2020).

Si photodiode Product FAQs, Japan, Dec. 23, 2005, [online], [Searched on Aug. 16, 2019], internet, <URL:https://www.hamamatsu.com/jp/ja/support/faqs/product-faqs/si-photodiodes/index.html> (with English Machine translation thereof obtained Aug. 17, 2020).

\* cited by examiner

CELL-HOLDING SUBSTRATE HOLDER FOR PREPARING OBSERVATION SPECIMEN, KIT INCLUDING SAME, AND OBSERVATION SPECIMEN PREPARATION METHOD

CROSS REFERENCE TO RELATED APPLICATIONS

This application is a national stage filing under section 371 of International Application No. PCT/JP2016/077056, filed on Sep. 14, 2016, and published on Mar. 23, 2017 as WO 2017/047617, which claims priority to Japanese Patent Application No. 2016-114067, filed on Jun. 8, 2016 and Japanese Patent Application No. 2015-180833, filed on Sep. 14, 2015 and Japanese Patent Application No. 2015-180832, filed on Sep. 14, 2015. The entire contents of each of said applications are hereby incorporated herein by reference.

TECHNICAL FIELD

The present invention relates to a cell-holding substrate holder, which can be used in preparing an observation specimen that is prepared by staining cells with various staining agents and for the purpose of observation with a microscope (optical microscope or fluorescence microscope); and a kit including the same; and a method of preparing an observation specimen, more particularly, a method of preparing an observation specimen obtained by carrying out wet fixing followed by staining (Papanicolaou stain, PAS stain, Alcian blue stain, or the like) using a staining bath, among pathological staining performed in cytology (cytological diagnosis).

BACKGROUND ART

The art is used mainly for a diagnosis of cancer, and carried out in accordance with a procedure in which an observation specimen is prepared from cells collected from a patient, and a person qualified as a cytotechnologist, a cytopathologist, a pathologist or the like examines the cells with a microscope to detect abnormal cells (atypical cells). In addition, the art is carried out mainly in medical institutions such as hospitals, and requires preparation and examination of a large amount of specimens (observation specimens and microscopic examination specimens) every day.

Cytology is classified according to a method for a collection of cells, and include exfoliative cytology in which a body fluid containing exfoliated cells is collected (sputum, urine, pleural effusion, ascites, pericardial effusion, cerebrospinal fluid, bile and so on), brush cytology in which a brush, a swab or the like is inserted into a body, and a lesioned part is abraded to collect cells (uterine cervix/body, bronchus, bile duct, pancreatic duct and so on), and fine needle aspiration cytology in which a thin needle is stuck to a lesioned part, and the lesioned part is sucked to collect cells (mammary gland, thyroid gland, lymph node, liver and so on). The collected cells are applied to an observation base plate (slide glass) to prepare an observation specimen. The smearing of cells to a slide glass is often performed with the cells dispersed in a liquid, and when the state of collected cells is not a liquid state such as that of a body fluid, cells may be dispersed in a fixing solution, and then applied (liquid-based cytology).

The "cell staining" is applied to various arts in addition to the above-described art. The staining method, reagent, device and equipment considerably vary depending on a use purpose (degree of completion) of a prepared observation specimen. As a purpose of staining, for example, a tissue is stained in different colors for each cell species to reveal localization of each cell species (e.g. immune tissue staining), only the number and staining intensity of target cells are detected by an apparatus on the basis of some markers and morphological characteristics of the cells (e.g. high-content screening and flow cytometry), observation is visually performed in the foregoing purpose (e.g. cell count using a blood cell counting chamber), a target substance inside and outside a cell is stained to observe localization (e.g. fluorescence microscope), the shape and the color of a cell organelle are observed (e.g. cytology), or further a structure of the inside of a cell organelle is observed in detail (e.g. electron microscope observation). Particularly, in this field, observation is performed by optical microscope observation, and it is required to acquire an observation image in which the shape and the staining color and gray level of a cell organelle can be discriminated at an observation magnification (about 200 to 400) which ensures that the cell organelle can be sufficiently observed.

In addition, for the reason of the state of a cell sample to be provided, properties of reagents to be used, and the degree of completion of a specimen to be required, a process for preparation of a conventional observation specimen in the art requires the following unique operation processes that are not carried out in other staining arts.

Smearing

This is an operation of smearing a cell sample to an observation base plate (slide glass). There are methods in which a cell sample is directly applied to a slide glass (wedge method, two step pull method, centrifugal preparation and so on), and a method in which cells are collected by a filter, and then transferred to a slide glass (membrane-filter method). The former methods, i.e. the wedge method and two step pull method, are convenient, but have a problem that since it is difficult to smear cells over a narrow area, and cells also stick to a glass used for rubbing, and thus, cell density decreases, and a wide area must be observed in observation operation. In addition, the latter method, i.e. the membrane-filter method has a problem that since not all of the collected cells can be transferred to a slide glass, cells are wasted, and the cell shape is degenerated under a pressure during a transfer operation.

Wet Fixation

This is an operation of immersing cells in a reagent (fixing solution) to fix the cells so that the applied cells are not degenerated. In the art, wet fixation is important, and when cells are dried and degenerated, the staining property is changed, so that diagnosis is affected. Generally, cells applied to a slide glass must be subjected to wet fixation within several seconds. Thus, it is difficult to smear a large amount of specimens at a time. In addition, the centrifugal preparation and membrane-filter method using equipment for smearing have a problem where cells are dried during the removal of the cells from equipment or a slide glass folder, and during a transfer operation in the case of the membrane-filter method. In addition, there is a problem where cells immediately after smearing are easily detached from a slide glass, and many cells are detached from the slide glass when immersed in a fixing solution. When cells have a massive overlapping property, it is further difficult to hold the cells on a slide glass. For solving the problem of detachment, a slide glass provided with a cell detachment preventing coating (silane coating or the like) has been devised, but in practice, a sufficient effect has not been obtained. In addition, for solving both the problems of detachment and drying, a method has been devised in which a fixing solution having a moisture retaining property is sprayed or dropped to coat cells and a slide glass. However, cells are detached at the moment when a fixing solution is sprayed, and there arises an additional problem where cells are coated with a moisture retaining component (PEG etc.), and therefore the staining property of cells is changed, so that diagnosis is affected.

Staining (Including Solvent Replacement, Separation and Coloring)

Several sheets of slide glass after completion of smearing and wet fixation are perpendicularly set in a staining basket, and put in a staining bath containing reagents such as a staining liquid or a pad filled with tap water, and is left standing, or sunk and lifted. The staining process is long and complicated, and for example, in a method of Papanicolaou stain, triple staining is performed, and about 20 to 25 steps are required in the whole process although the number of steps somewhat varies depending on an executing facility. This is because the staining process includes not only staining, but also a step of replacing a solvent in conformity to a staining reagent, a washing step (separation) of washing off an extra staining liquid, and a step of immersing the sample in a solution for performing coloring. In addition, it is preferable that the time of each staining step, and the frequency with which the sample is sunk and lifted in a reagent are strictly set, and in staining in the art in which a target such as a cell organelle is stained in different colors, the above-mentioned requirement is important for attaining stability and reproducibility of staining. Thus, in staining in the art, a large amount of patient specimens are evenly and quickly treated to perform staining with stability and reproducibility, and use of a staining basket and a staining bath at this time is helpful. The staining basket is capable of holding a plurality of a slide glass without scratching the smeared surface, so that operations such as movement between staining baths and sinking and lifting are facilitated. In addition, it is required to quickly immerse the smeared surface in a large volume of a staining liquid and a separation liquid (washing liquid) so that staining unevenness and destaining unevenness do not occur, and such unevenness can be avoided by operations of putting and sinking and lifting the sample with the staining basket and the staining bath. Thus, in the staining process, the sample is brought into contact with a reagent over many steps, and therefore there is a problem where cells applied to a slide glass are detached as in the case of the wet fixation process.

Dehydration and Clearing

The sample is transferred from a low-concentration alcohol bath to a pure alcohol bath stepwise to be dehydrated, and is finally immersed in a xylene bath. This operation makes the tissue transparent, so that a specimen suitable for microscopic examination is obtained. For clearing, a solvent having high dissolving power is used, and therefore when cells on a polycarbonate membrane that is used mainly in a membrane-filter method are cleared as such, the membrane is dissolved, so that turbidity occurs, and therefore the membrane cannot be used as an observation substrate. Thus, it is necessary to transfer the collected cells onto a slide glass.

Mounting

A mounting medium (resin dissolved in a solvent) is put on the smeared surface, and cells are sandwiched between a cover glass and a slide glass. By sealing the stained cells with the mounting medium, physical impact on the smeared surface during a microscopic examination operation, degradation due to microscope illumination, and discoloration with time can be prevented to store the cells for a long period of time.

Observation

Observation is performed with an optical microscope. For example, it is necessary to observe a nuclear chromatin structure in Papanicolaou stain and the color of granules in PAS stain, and therefore a clear observation image with a magnification of at least 200 to 400 should be obtained.

Preparation of a conventional observation specimen in the art is performed by a step as described above. Such a staining process using a staining basket and a staining bath is carried out manually, or by an automatic staining apparatus.

In addition, preparation of a previously known observation specimen in the art has been performed by smearing cells to a slide glass. The slide glass has such an advantage that since the slide glass has a favorable observation property, and cells are distributed in such a manner as to be attached to a glass surface in a slightly widened state, the inside of a cell is easily observed, and since the slide glass is flat, the mounting operation is facilitated. On the other hand, due to the flat structure of the slide glass, cells cannot be held, and are thus detached in the process for preparing an observation specimen. In addition, the slide glass has a poor moisture retaining property, so that cells are easily degenerated by drying. Further, there is the problem that since cells have a flat shape, it is difficult to detect a cell shape characteristic of cancer cells and a three-dimensional cellular atypia. Thus, a method for preparing an observation specimen enabling a cell organelle to be sufficiently observed with an optical microscope while solving all three problems: cell detachment, drying and loss of three-dimensional properties, has not been devised heretofore.

Note that methods in which using a filter, cells are collected to prepare a specimen for analysis or diagnosis have been devised as described below, but these methods cannot solve the above-mentioned problems.

Patent Literature 1 discloses a method for avoiding errors during mounting and eliminating the need for expert skills, but does not disclose a structure and type of a filter.

Patent Literatures 2 to 5 do not disclose a method for preparing an observation specimen using a staining bath. In addition, a mounting process is not carried out, cells are not mounted with a mounting medium having a refractive index comparable to that of the sample, a curved fiber surface causes irregular reflection, and therefore an observation image so clear that cell organelles can be discriminated in an optical microscope cannot be obtained. In fact, in an example in Patent Literature 2, the presence/absence of cells having a specific cell marker is merely examined by fluorescence observation, and in an example in Patent Literature 3, the number of cells is merely counted on the basis of the outer shape of cells and the presence/absence of stains in an unclear image with a low magnification. Thus, an observation specimen having a degree of completion, which is required in the art, cannot be obtained with a method in which a mounting process is not carried out when cells collected on a fiber are observed.

On the other hand, when a filter with cells collected thereon is observed on a microscope stage, it is preferable that only a filter is removed from a filtration apparatus or the like, and placed on a thin base plate such as a slide glass to complete an observation specimen. As the reason for this, the mounting operation must be carried out, and when cells are observed at a high magnification, a distance between an objective lens and an object to be observed decreases, and therefore it is necessary to thinly finish the observation specimen as a whole. Note that the mounting operation is carried out by sealing cells with an oily substance mainly composed of glycerin or liquid paraffin, or a reagent called a mounting medium and composed of a resin dissolved in a solvent, for preventing physical damage to a cell solidification surface during microscope operation, damage due to microscope illumination, and discoloration with time. Since ingress of air bubbles, etc., during mounting deteriorates an observation property, cells are sandwiched between two flat glasses (slide glass and cover glass), and gaps are sealed with a mounting medium so that air bubbles hardly stick to and remain on a mounting surface.

In a specimen holder disclosed in Patent Literature 4, a window capable of collecting cells can be removed, but a method for fixing the window during the collection of cells, a method for removing the window, and a mechanism thereof, are not described in detail. Thus, with a filter holder that is not capable of easily attaching/detaching only a filter, an observation specimen having a degree of completion, which is required in the art, cannot be obtained.

In addition, in a filtration module disclosed in Patent Literature 5, a filter is bonded to a frame (resin frame) with an adhesive for retaining a filter shape during the collection of cells, and cannot be easily attached/detached. Therefore, when the filter with cells collected thereon is sandwiched between glasses together with the frame, and mounted, not only air bubbles easily remain on a level difference portion between the filter and the frame, but also a mounting medium undergoes volume reduction as it is dried, and therefore gaps are generated between the upper and lower glasses, so that air bubbles are generated, leading to a deterioration of an observation property. Moreover, the observation specimen itself has an increased thickness, so that microscopic examination at a high magnification is impossible. Thus, it is necessary to remove only the filter from the frame, but in this case, only the filter cannot be removed unless a complicated operation such as the cutting of the filter is carried out, and in the cutting operation, the filter may be distorted, resulting in a detachment of cells fixed to the filter.

CITATION LIST

Patent Literature

[Patent literature 1] Japanese Unexamined Patent Publication (Kokai) No. 4-165321
[Patent literature 2] Japanese Unexamined Patent Publication (Kokai) No. 2012-75383
[Patent literature 3] Japanese Unexamined Patent Publication (Kokai) No. 2004-298158
[Patent literature 4] Japanese Translation Publication (Kohyo) No. 11-507724
[Patent literature 5] Japanese Translation Publication (Kohyo) No. 2008-537485

SUMMARY OF INVENTION

Technical Problem

Therefore, an object of the present invention is to provide a cell-holding substrate holder and a kit for preparing a cell observation specimen, wherein the cell-holding substrate, such as a filter or the like, can be easily attached and detached, and to provide a method of preparing an observation specimen, wherein cell organelles can be satisfactorily observed using an optical microscope, while three problems of cell detachment, drying, and loss of the three-dimensional properties can be simultaneously solved.

Solution to Problem

The object can be solved by the following present inventions:

[1] a cell-holding substrate holder for preparing an observation specimen, said holder comprising:
(1) a support plate having a cell-holding substrate arrangement portion having a window portion through which water can pass, and
(2) a removable sandwiching plate which has a window portion through which water can pass, and is capable of working in conjunction with the support plate to sandwich and fix a cell-holding substrate in the cell-holding substrate arrangement portion;
[2] the cell-holding substrate holder for preparing an observation specimen of [1], wherein the support plate has the cell-holding substrate arrangement portion and a frame portion;
[3] the cell-holding substrate holder of [1] or [2], wherein the support plate has hollows (preferably through-holes) on both sides of the window portion, and the sandwiching plate is a cover plate having claws which can be fitted into both of the hollows (preferably through-holes);
[4] the cell-holding substrate holder of [2], wherein the sandwiching plate is a flange plate having a flange portion capable of abutting to the frame portion of the support plate, and the cell-holding substrate holder further comprises a clip capable of sandwiching and fixing the frame portion of the support plate and the flange portion of the flange plate;
[5] the cell-holding substrate holder of [4], wherein the flange plate has a cup portion, which a sample can be put into, and can communicate with the window portion of the flange portion;
[6] the cell-holding substrate holder of [5], wherein the cup portion can be separated;
[7] the cell-holding substrate holder of any one of [3] to [6], comprising the cover plate, the flange plate, and the clip;
[8] the cell-holding substrate holder of any one of [1] to [7], wherein the window portion of the support plate is provided with a support member capable of supporting the cell-holding substrate;
[9] the cell-holding substrate holder of any one of [1] to [8], wherein a shape and a size of the support plate is a rectangle which can be accommodated in a staining basket;
[10] the cell-holding substrate holder of any one of [1] to [9], wherein the support plate and/or the sandwiching plate is provided with a hollow (preferably a through-hole) into which a tweezer tip can be inserted;
[11] the cell-holding substrate holder of any one of [1] to [10], wherein all materials are made of organic resin;
[12] the cell-holding substrate holder of [1] or [2], wherein the sandwiching plate is a cover plate which can be fitted, clamped, or pivotably attached to the support plate;
[13] the cell-holding substrate holder of any one of [3] and [7] to [12], wherein the cover plate has a power point portion capable of applying a force;
[14] the cell-holding substrate holder of any one of [3] and [7] to [13], wherein the cell-holding substrate arrangement portion of the support plate and/or the cover plate has a liquid-passage structure;
[15] a kit for preparing an observation specimen, comprising the cell-holding substrate holder of any one of [1] to [14], and a cell-holding substrate;

[16] the kit of [15], wherein the cell-holding substrate is an inorganic fiber sheet having a porosity of 90% or more;
[17] the kit of [15] or [16], wherein a shape and a size is a rectangle which can be accommodated in a staining basket, when the cell-holding substrate is attached to the cell-holding substrate holder; and
[18] a method of preparing an observation specimen, comprising collecting cells with an inorganic fiber aggregate, performing wet fixation of the cells as they are, staining the cells, and mounting the cells with a mounting medium having a refractive index equivalent to that of the inorganic fiber.

Advantageous Effects of Invention

According to the cell-holding substrate holder of [1] in the present invention, the cell-holding substrate can be sandwiched and fixed by the support plate and the sandwiching plate, and the cell-holding substrate can be easily removed from the support plate. Therefore, only the cell-holding substrate can be transferred onto a slide glass, a stable mounting operation is possible, and the whole observation sample can be thinly finished.

According to the cell-holding substrate holder of [2] in the present invention, the support plate has a frame portion, and various functions can be added by providing the frame portion with a fitting hollow for detachably fixing the sandwiching plate, a hollow into which a tweezer tip can be inserted in the recovery of the cell-holding substrate, an accommodation hollow capable of accommodating a protrusive portion of the sandwiching plate, or the like.

According to the cell-holding substrate holder of [3] in the present invention, the cell-holding substrate can be fixed to the support plate by claws of the cover plate, and therefore, a shearing force is not applied to the cell-holding substrate. Thus, even when an inorganic cell-holding substrate made of glass or the like (for example, an inorganic fiber sheet) is used, there is no risk of breakage, and it is easy to attach and detach the cell-holding substrate. In addition, the cell-holding substrate holder has the cover plate, and can be used in a staining process using a staining basket, while the cover plate works in conjunction with the support plate to sandwich and fix the cell-holding substrate in the cell-holding substrate arrangement portion, and is therefore excellent in workability.

According to the cell-holding substrate holder of [4] in the present invention, the cell-holding substrate can be fixed to the support plate by clips, and therefore, a shearing force is not applied to the cell-holding substrate. Thus, even when an inorganic cell-holding substrate made of glass or the like (for example, an inorganic fiber sheet) is used, there is no risk of breakage, and it is easy to attach and detach the cell-holding substrate.

According to the cell-holding substrate holder of [5] in the present invention, even a large amount of a liquid-based cell sample can be filtered to collect cells when the cell-holding substrate is used as a filter.

According to the cell-holding substrate holder of [6] in the present invention, the cup portion can be separated, and therefore, the volume of the kit can be reduced.

According to the cell-holding substrate holder of [7] in the present invention, the cell-holding substrate holder can be used in a staining process using a staining basket, while the cover plate and the flange plate work in conjunction with the support plate to sandwich and fix the cell-holding substrate in the cell-holding substrate arrangement portion, and is therefore excellent in workability. Also, a shearing force is not applied to the cell-holding substrate, and therefore, the cell-holding substrate can be attached and detached without breaking the cell-holding substrate.

According to the cell-holding substrate holder of [8] in the present invention, the window portion of the support plate is provided with a support member capable of supporting the cell-holding substrate, and therefore, the cell-holding substrate is hardly broken under water pressure associated with operations, such as cell filtration, staining, or the like.

According to the cell-holding substrate holder of [9] in the present invention, the support plate can be accommodated in a staining basket, and therefore, the cell-holding substrate holder can be applied to a staining basket or an automatic staining apparatus which have been conventionally used for staining cells smeared on a slide glass.

According to the cell-holding substrate holder of [10] in the present invention, the cell-holding substrate can be attached and detached using tweezers, and therefore, workability is improved, and the risk of scratching the cell-holding substrate with a tweezer tip is reduced.

According to the cell-holding substrate holder of [11] in the present invention, the cell-holding substrate holder is made of organic resin, and therefore, the cell-holding substrate holder is easily discarded after use.

According to the cell-holding substrate holder of [12] in the present invention, the cell-holding substrate can be fixed to the support plate by fitting, clamping, or pivotably attaching the cover plate, and therefore, a shearing force is not applied to the cell-holding substrate. Thus, even when an inorganic cell-holding substrate made of glass or the like (for example, an inorganic fiber sheet) is used, there is no risk of breakage, and it is easy to attach and detach the cell-holding substrate. In addition, the cell-holding substrate holder can be used in a staining process using a staining basket, while the cover plate works in conjunction with the support plate to sandwich and fix the cell-holding substrate in the cell-holding substrate arrangement portion, and is therefore excellent in workability.

According to the cell-holding substrate holder of [13] in the present invention, the cover plate has a power point portion capable of applying a force, and the sandwiching and fixing action by the cover plate and the support plate can be cancelled by applying a force to the power point portion. Therefore, the cell-holding substrate can be easily attached and detached without breaking the cell-holding substrate. For example, when the power point portion is a protrusive portion which can be hooked with a finger, or a cut-out portion into which a finger can be inserted, the sandwiching and fixing action by the cover plate and the support plate can be cancelled by applying a force to the protrusive portion or the cut-out portion, and the cell-holding substrate can be easily attached and detached without breaking the cell-holding substrate.

According to the cell-holding substrate holder of [14] in the present invention, the cell-holding substrate arrangement portion and/or the cover plate has a liquid-passage structure, and therefore, it is possible to promote the washing and removal of a residual staining liquid, which is easily generated during staining in a part of the cell-holding substrate sandwiched and fixed by the cover plate and the cell-holding substrate arrangement portion. Thus, the residual staining liquid is diffused, so that staining unevenness hardly occurs, and therefore an observation specimen with excellent observation properties with a microscope can be prepared.

According to the kit of [15] in the present invention, the cell-holding substrate can be sandwiched and fixed by the support plate and the sandwiching plate, and the cell-holding substrate can be easily removed from the support plate. Therefore, only the cell-holding substrate can be transferred onto a slide glass, a stable mounting operation is possible, and the whole observation sample can be thinly finished. In addition, when the cell-holding substrate is a porous sheet, expensive equipment and a special technique are not required, and floating cells can be concentrated and fixed on the cell-holding substrate in a pseudo manner, in a one-step operation of cell filtration by gravity, to prepare a cell observation specimen.

According to the kit of [16] in the present invention, the cell-holding substrate is made of an inorganic fiber sheet, and cells can be held in internal voids of the cell-holding substrate. Therefore, as with cells in an adhesive state, the operation of immersing cells in a reagent can be carried out. In addition, the porosity is 90% or more, and therefore, not only is it easy to hold cells in internal voids of the cell-holding substrate, but it is also excellent in water permeability.

According to the kit of [17] in the present invention, the cell-holding substrate holder to which the cell-holding substrate is attached can be accommodated in a staining basket. Therefore, cells can be stained with good operability by applying the cell-holding substrate holder to a staining basket or an automatic staining apparatus which have been conventionally used for staining cells smeared on a slide glass.

According to the method of preparing an observation specimen of [18] in the present invention, cells are stably held in internal voids of an inorganic fiber aggregate excellent in rigidity, and therefore, cell detachment and the loss of the three-dimensional properties can be prevented. In addition, the method is also useful for holding a cell mass having stratification properties.

In addition, inorganic fibers are hydrophilic, and the inorganic fiber aggregate has a certain degree of water-holding capacity. Therefore, cells are not dried even if left for several minutes, and stable wet fixation becomes possible. Thus, the method is useful for simultaneous preparation of a large amount of specimens, or application to equipment.

Further, the three-dimensional properties of cells are retained, and therefore, the method is useful for observation of three-dimensional cellular atypia, or a cell mass having stratification properties.

Further, the inorganic fiber aggregate exhibits chemical resistance to a solvent (ethanol, methanol, or xylene) contained in a reagent to be used in cytology, and therefore, after cell collection, can be used directly as a substrate for observation, and mounted, and therefore, a transfer operation that is carried out in a conventional membrane-filter method using a membrane filter is unnecessary. Thus, there is no risk of degeneration of the cell shape due to the pressure of the transfer, and cell loss that occurs at this time is eliminated. In addition, since mounting is performed with a mounting medium having a refractive index equivalent to that of the fiber, irregular reflection caused by a curved fiber surface is suppressed, and therefore, an observation image so clear that cell organelles can be discriminated in an optical microscope can be obtained.

DESCRIPTION OF EMBODIMENTS

Hereinafter, with reference to the drawings, as an embodiment of the cell-holding substrate holder for preparing an observation specimen of the present invention, a filter holder for preparing an observation specimen for floating cells (hereinafter sometimes referred to as the filter holder of the present invention), in which the cell-holding substrate acts as a filter, and as an embodiment of the kit, including the same, for preparing an observation specimen of the present invention, a filter kit (hereinafter sometimes referred to as the kit of the present invention) will be explained, and then, the method of preparing an observation specimen of the present invention will be explained.

The filter kit of the present invention comprises a filter for collecting cells, and the filter holder of the present invention. Hereinafter, the kit of the present invention will be explained, but the explanation will be applied to the filter holder of the present invention, except that the kit of the present invention comprises the filter.

Figure 1:
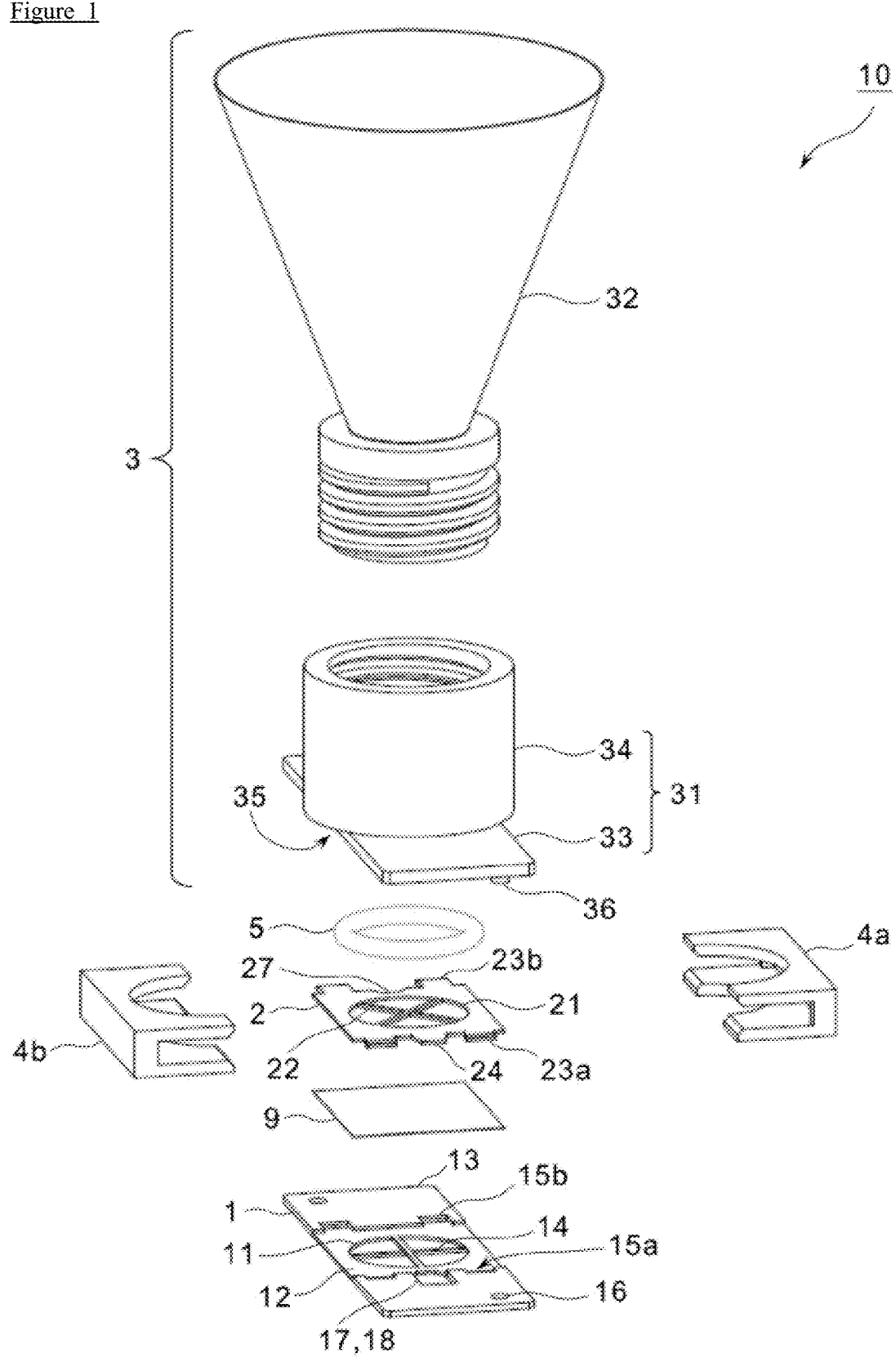
FIG. 1 is a perspective view schematically showing an embodiment of the filter kit of the present invention.

An embodiment of the kit 10 of the present invention shown in FIG. 1 is composed of a support plate 1; a cover plate 2; a flange portion 31 and a cup portion 32, which constitute a flange plate 3; two clips 4a, 4b; a packing 5; and a filter 9.

The support plate 1 has a filter arrangement portion 12 having a window portion 11 through which water can pass, and can further have a frame portion 13. The window portion 11 can be provided with a support member 14 capable of supporting the filter 9. The window portion 11 shown in FIG. 1 is provided with an X-shaped support member 14, but the kit of the present invention may be provided with other support members, for example, *-shaped, triangular shaped, I-shaped, Y-shaped, =-shaped, latticed shaped, mesh-shaped, or the like.

The frame portion 13 may be provided with fitting hollows 15a, 15b for detachably fixing a cover plate 2 on both sides of the window portion 11; connecting holes 16 for arranging the flange portion 31 at a predetermined position of the support plate 1; a hollow 17 into which a tweezer tip can be inserted in the recovery of the filter 9; an accommodation hollow 18 capable of accommodating a protrusive portion 24 of a cover plate 2 described below, or the like. In FIG. 1, the hollow 17 into which a tweezer tip can be inserted also serves as the accommodation hollow 18. As shown in FIG. 1, the fitting hollows 15a, 15b, the hollow 17, or the accommodation hollow 18 are preferably through-holes. The hollow 17 into which a tweezer tip can be inserted may be provided on a sandwiching plate, such as the cover plate 2 or the flange plate 3.

It is preferable that the hollow 17 into which a tweezer tip can be inserted is provided adjacent to the filter arrangement portion 12 so that the filter 9 can be taken out. In this way, if the hollows 17 into which a tweezer tip can be inserted are provided on both the support plate 1 and the sandwiching plate, when the sandwiching plate is detached, the filter 9 can be removed without breaking it, even if the filter 9 is attached to either the support plate 1 or the sandwiching plate. The protrusive portion 24 of the cover plate 2 can be accommodated in the accommodation hollow 18 so that no protrusion is formed on the filter holder, and therefore, conventionally, it is easy to use and accommodate the filter holder in a staining basket.

In FIG. 1, the filter arrangement portion 12 is formed as a concave portion having the same rectangular shape as the filter 9 and substantially the same area. Therefore, it is possible to accommodate the filter 9 in close contact with the filter arrangement portion 12, and it is possible to prevent the displacement of the filter 9. Further, in FIG. 6, the filter arrangement portion is formed as a concave portion having the same circular shape as the filter and substantially the same area. Therefore, it is possible to accommodate the filter in close contact with the filter arrangement portion, and it is possible to prevent the displacement of the filter. In this way, it is preferable that the filter arrangement portion is formed as a concave portion having the same shape as the filter and substantially the same area.

However, the filter arrangement portion may be formed as a concave portion having a shape different from the filter or a wider area than the filter, to the extent that filter displacement does not occur. In this case, a spatial margin is generated between the filter arrangement portion and the filter, and tweezers can be interposed between the filter arrangement portion and the filter, and therefore, it is easy to arrange the filter in the filter arrangement portion, and it is easy to remove the filter from the filter arrangement portion, without breaking it. For example, in the case of a circular filter, the filter arrangement portion may be formed as a concave portion having a rectangular shape with a longitudinal length and a lateral length equal to or greater than the diameter of the filter, and tweezers can be interposed in the space formed between the filter arrangement portion and the filter, and therefore, the filter can be attached and detached without breaking it.

In connection with this, if the filter arrangement portion may be formed as a concave portion having a shape different from the filter or a wider area than the filter, and there is a possibility that filter displacement will occur, it is preferable that the filter arrangement portion is provided with a convex portion at a position capable of contacting with the outer edge of the filter, so that filter displacement can be prevented by partially making contact with the outer edge of the filter.

Figure 6:
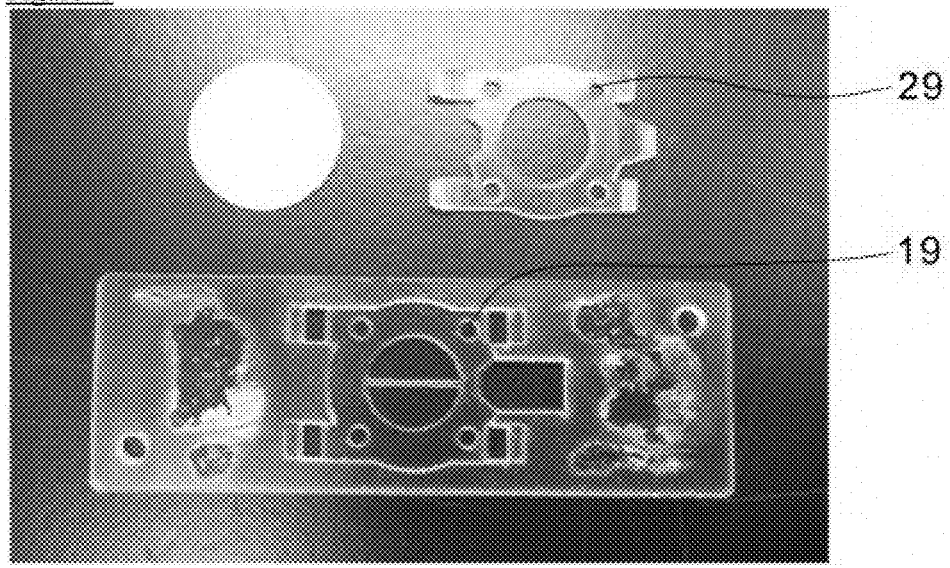
FIG. 6 is a photograph, in place of drawings, showing the state before the use (the state before holding a filter) of still another embodiment of the filter kit (a support plate, a cover plate, and a filter) of the present invention.

Further, as shown in FIG. 6, it is preferable that the filter arrangement portion 12 is provided with through-holes 19, as a liquid-passage structure. This is because liquid permeability is improved due to such through-holes, and in the washing step after the staining step, the washing liquid reaches the filter 9, and is easily drained after washing, and therefore, residual staining liquid can be easily removed by washing. That is to say, if the staining liquid remains in a part of the filter sandwiched by the cover plate 2 and the filter arrangement portion 12, the staining liquid is diffused, so that uneven staining occurs, and therefore observation properties with a microscope are lowered. However, due to the liquid-passage structure (through-holes 19), it is easy to remove the residual staining liquid by washing, and therefore, an observation specimen with excellent observation properties with a microscope can be prepared.

Further, the liquid-passage structure in FIG. 6 is a group of through-holes 19, but it is not limited to such through-holes, and it may be a group of grooves, which are provided on the surface in contact with the filter, and lead to the outer edge (including the fitting hollows 15a, 15b and the hollow 17) of the filter arrangement portion 12. When the liquid-passage structure is a group of grooves, liquid permeability is improved due to the grooves, and therefore, the grooves exhibit the same effect as the case of the through-holes, and an observation specimen with excellent observation properties with a microscope can be prepared.

As described below, when a packing 5 capable of preventing liquid leakage is provided between the window portion 35 of the flange plate 3 and the window portion 11 of the support plate 1 (the window portion 21 of the cover plate 2 when the cover plate 2 is used), it is preferable that the liquid-passage structure (through-holes 19, grooves, or the like) is located outside the position where the packing 5 is in contact, so that leakage of floating cells is prevented during cell filtration.

The cover plate 2 has a window portion 21 through which water can pass, and the window portion 21 may be provided with a support member 22 capable of supporting the filter 9. The shape of the support member 22 may be X-shaped, *-shaped, triangular shaped, I-shaped, Y-shaped, =-shaped, latticed shaped, mesh-shaped, or the like. The support member 22 of the cover plate 2 need not be the same shape as the support member 14 of the support plate 1.

Figure 3:
FIG. 3 is a photograph, in place of drawings, showing the state of holding a filter by sandwiching the filter between the support plate and the cover plate, which are shown in FIG. 2.

The cover plate 2 may be provided with fitting claws 23a, 23b which can be fitted into both of the fitting hollows 15a, 15b of the support plate 1. As shown in FIG. 3, the cover plate 2 works in conjunction with the support plate 1 to sandwich and fix the filter 9 in the filter arrangement portion 12 of the support plate 1. More particularly, after the filter 9 is disposed in the filter arrangement portion 12 of the support plate 1, the fitting claws 23a, 23b of the cover plate 2 are fitted into the fitting hollows 15a, 15b, and the filter 9 can be sandwiched and fixed by the support plate 1 and the cover plate 2. Therefore, a shearing force is not applied to the filter, and even when an inorganic filter made of glass or the like (for example, an inorganic fiber sheet) is used, there is no risk of breakage.

Further, the cover plate 2 shown in FIG. 1 has a protrusive portion 24 which can be hooked with a finger, and therefore, the cover plate 2 can be easily removed from the support plate 1 by hooking the protrusive portion 24 with a finger and pulling it upwards, and the filter 9 can be detached without breaking it. In particular, in FIG. 1, the cover plate 2 has the protrusive portion 24 which can be hooked with a finger, and further, the length of one fitting claw (23a in FIG. 1) of the cover plate 2 is shorter than that of another fitting claw (23b in FIG. 1), and the fitting state of the fitting claw 23a into the fitting hollow 15a is shallow, and therefore, the cover plate 2 can be easily removed by hooking the protrusive portion 24 with a finger and pulling it upwards, and the filter 9 can be detached without breaking it.

Further, the protrusive portion 24 of the cover plate 2 is smaller than the accommodation hollow 18 of the support plate 1, and a gap is generated between the protrusive portion 24 and the accommodation hollow 18 in the state of mounting the cover plate 2 on the support plate 1, and therefore, the cover plate 2 can be easily removed from the support plate 1 by inserting a finger into the gap and hooking the protrusive portion 24 with a finger and pulling it upwards, and the filter 9 can be detached without breaking it.

The protrusive portion 24 of the cover plate 2 shown in FIG. 1 is a power point portion which projects in the plane direction of the cover plate 2, but the protrusive portion may project in the thickness direction of the cover plate 2, instead of the plane direction. In the case of such a power point portion projecting in the thickness direction, by pulling the power point portion with fingers, the filter 9 can be released from sandwiching by the cover plate 2 and the support plate 1, and detached without breaking the filter.

Further, FIG. 1 shows an embodiment having the protrusive portion 24, in which the power point portion of the cover plate 2 can be hooked with a finger, but instead of the protrusive portion 24, another embodiment may have a power point portion consisting of a cut-out portion into which a finger can be inserted. In the case of such a cut-out portion, by inserting a finger into the cut-out portion, and pulling it upwards by hooking the cover plate 2 with fingers, the filter 9 can be released from sandwiching by the cover plate 2 and the support plate 1, and detached without breaking the filter. It is preferable that the cut-out portion extends from the outer edge of the cover plate 2 toward the window portion 21. Further, in the thickness direction of the cover plate, the cut-out portion may be completely cut-out (i.e., a through-hole), or partially cut-out (i.e., a hollow).

It is preferable that the support member 22 of the cover plate 2 is arranged so as not to overlap with the support member 14 of the support plate 1, so that the load on the filter 9 can be distributed, while supporting the filter 9 against water pressure from both directions of the filter surfaces, generated during the staining step described below.

Figure 2:
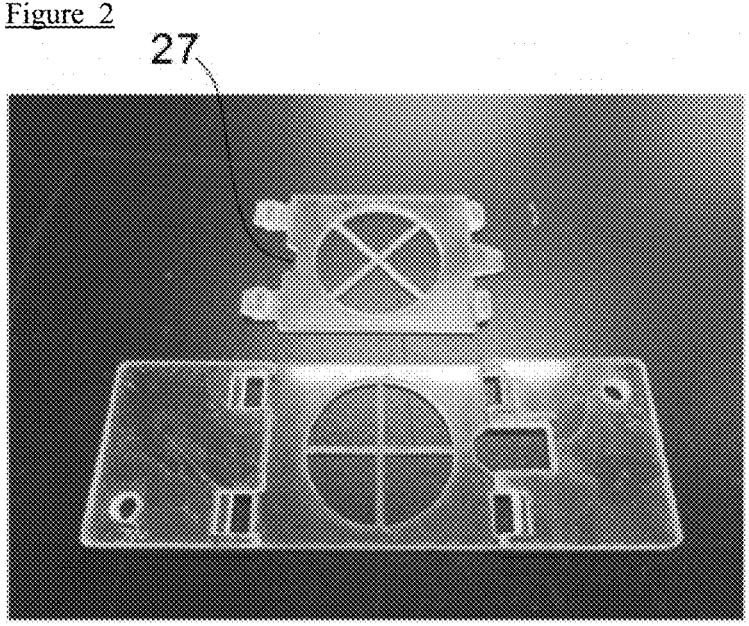
FIG. 2 is a photograph, in place of drawings, showing the state before the use (the state before holding a filter) of an embodiment of the filter holder (a support plate and a cover plate) of the present invention, which is included in the filter kit of the present invention shown in FIG. 1.

Further, as shown in FIGS. 1 and 2, the cover plate 2 has a hollow 27, into which a tweezer tip can be inserted, between the fitting claws 23b and adjacent to the window portion 21, and therefore, when the cover plate 2 is removed from the support plate 1, even if the filter 9 is attached to the cover plate 2, the filter 9 can be removed without breaking it.

In FIGS. 1 and 6, the outer shape of the cover plate 2 corresponds to the outer shape of the filter arrangement portion 12 of the support plate 1, and the cover plate 2 can be accommodated in the filter arrangement portion 12. Therefore, the filter 9 can be sandwiched and fixed by the filter arrangement portion 12 and the cover plate 2, and it is possible to prevent the displacement of the filter 9. In this way, the outer shape of the cover plate 2 corresponds to the outer shape of the filter arrangement portion, and it is preferable that the cover plate 2 can be accommodated in the filter arrangement portion 12.

Further, as described above, when the filter arrangement portion 12 has the convex portion, the cover plate 2 has a concave portion at the position corresponding to the convex portion, and it is preferable that the convex portion can be accommodated in the concave portion. This is because the thickness of the filter arrangement portion 12 at the time of attaching the cover plate 2 can be made approximately equal to that of the frame portion 13 by such an accommodation structure, and therefore, conventionally, it is easy to use and accommodate the filter holder in a staining basket.

Further, as shown in FIG. 6, it is preferable that the cover plate 2 has through-holes 29 as the liquid-passage structure. This is because it acts in the same manner as the case where the filter arrangement portion 12 of the support plate 1 has the through-holes 19, and therefore, an observation specimen with excellent observation properties with a microscope can be prepared.

Further, the liquid-passage structure of the cover plate 2 in FIG. 6 is a group of through-holes 29, but it is not limited to such through-holes, and it may be a group of grooves, which are provided on the surface in contact with the filter, and lead to the outer edge of the cover plate. When the liquid-passage structure is a group of grooves, liquid permeability is improved due to the grooves, and therefore, the grooves exhibit the same effect as the case of the through-holes, and an observation specimen with excellent observation properties with a microscope can be prepared.

Further, as similar to the case where the filter arrangement portion 12 of the support plate 1 has the liquid-passage structure, as described below, when a packing 5 capable of preventing liquid leakage is provided between the window portion 35 of the flange plate 3 and the window portion 21 of the cover plate 2, it is preferable that the liquid-passage structure (through-holes 29, grooves, or the like) is located outside the position where the packing 5 is in contact, so that leakage of floating cells is prevented during cell filtration.

The liquid-passage structure in the filter arrangement portion of the support plate 1 may be the same as, or different from the liquid-passage structure in the cover plate 2. For example, with respect to the shape, size, or position of the liquid-passage structure, through-holes or grooves, or the like, they may be the same or different. However, as shown in FIG. 6, it is preferable that the liquid-passage structure in the filter arrangement portion of the support plate 1 and the liquid-passage structure in the cover plate 2 are disposed at opposite positions. This is because, due to the arrangement at the opposite positions, the washing liquid reaches the filter, and is easily drained after washing, and therefore, it is easy to prevent the staining liquid from remaining, and an observation specimen with excellent observation properties with a microscope can be prepared. The liquid-passage structure may be provided only in the filter arrangement portion of the support plate 1, or only in the cover plate 2, but when the liquid-passage structures are provided in both positions, it is excellent in the above-mentioned effects.

In the filter holder shown in FIG. 1, the support plate 1 has both fitting hollows 15a, 15b, which face each other across the window portion 11 in the longitudinal direction, and can sandwich and fix the filter 9 by fitting the fitting claws 23a, 23b of the cover plate 2 into the fitting hollows 15a, 15b. However, the fitting positions need not face each other across the window portion 11 of the support plate 1 in the longitudinal direction. For example, the fitting positions may face each other across the window portion 11 of the support plate 1 in the lateral direction. Alternatively, with reference to the center of the window portion 11, the fitting positions may be arranged so that the angle formed by adjacent fitting positions is a fixed angle, such as 60°, 72°, 90°, 120°, or the like.

Further, in the embodiment shown in FIG. 1, the support plate 1 has four fitting hollows, which are involved in fitting, and the cover plate has four fitting claws, which correspond to the fitting hollows. However, the fitting positions are not limited to four positions, so long as the fitting can be carried out at two or more positions. It is preferable that the fitting can be carried out at three to six positions, so that the filter 9 can be stably sandwiched and fixed.

Further, in the filter holder shown in FIG. 1, the filter 9 can be sandwiched and fixed by fitting the fitting claws 23a, 23b of the cover plate 2 into the fitting hollows 15a, 15b of the support plate 1. However, it is not necessary that the filter holder is an embodiment in which the cover plate 2 is mounted on the support plate 1 by fitting and the filter 9 can be sandwiched and fixed. For example, the filter holder may be an embodiment, wherein it includes a cover plate having a window portion through which water can pass, and a support plate having a filter arrangement portion having a window portion through which water can pass; the cover plate can be mounted on the filter arrangement portion; and the support plate and the cover plate can be clamped by thin-walled clips, which can sandwich the support plate and the cover plate, as described below. Alternatively, the filter holder may be an embodiment, comprising a cover plate that has a window portion through which water can pass, a pivotably-attachable shaft at one end, and a convex portion (protrusion or the like) or a concave portion (through-hole, hollow or the like) at the other end; and a support plate that has a filter arrangement portion having a window portion through which water can pass, a bearing at one end of the filter arrangement portion, and a concave portion (through-hole, hollow or the like) or a convex portion (protrusion or the like) at the other end thereof; wherein the cover plate and the support plate can be pivotably attached by inserting the pivotably-attachable shaft of the cover plate into the bearing of the support plate at one end; and wherein the convex and the concave can be fitted at the other end. Even in these embodiments, since a shearing force is not applied to the filter 9, the filter can be attached and detached without damaging the filter.

Even if the filter holder has the clampable cover plate or the pivotably-attachable cover plate, against the support plate 1, it is preferable that the cover plate has a power point portion, such as a protrusive portion which can be hooked with a finger, a protrusive portion which can be pinched with fingers, a cut-out portion into which a finger can be inserted, or the like, so that the filter can be easily detached without breaking it.

The shape and size of the support plate 1 is preferably a rectangle which can be accommodated in a staining basket, so that a staining basket and a staining bath, which are conventionally known, can be used. That is to say, it is preferably a shape and size according to a conventionally-known slide glass for preparing an observation specimen, and more particularly, it is preferably about 76 mm in length, about 26 mm in width, and about 1 mm in thickness. The cover plate is preferably a shape and size that do not protrude from the support plate, so that a staining basket and a staining bath, which are conventionally known, can be used.

Figure 4:
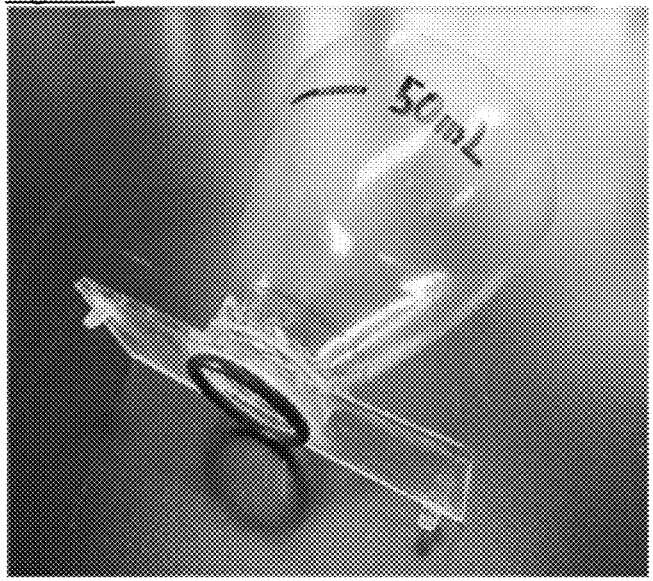
FIG. 4 is a photograph, in place of drawings, showing the state where a flange plate (a flange portion and a cup portion are integrated) and a packing, which are included in another embodiment of the filter kit of the present invention, are assembled.

The flange plate 3 comprises the flange portion 31, and the cup portion 32, which a sample can be put into, and can communicate with the window portion 35 of the flange portion 31. As shown in FIG. 1, it can be designed so that the flange portion 31 and the cup portion 32 can be separated from each other, or as shown in FIG. 4, it can be designed so that the flange portion and the cup portion are integrated.

The flange portion 31 shown in FIG. 1 has a window portion 35, through which water can pass, in the center of the flange plate, and comprises a flange 33 capable of abutting to the frame portion 13 of the support plate 1, and a connecting portion 34 capable of communicatively connecting the inside of the cup portion 32 and the window portion 35 of the flange portion 31. The flange 33 can be provided with connecting protrusions 36 at the positions corresponding to connecting holes 16 of the support plate 1, so that the flange portion 31 is disposed at a predetermined position with respect to the support plate 1.

Figure 5:
FIG. 5 is a photograph, in place of drawings, showing the state where the filter kit of the present invention shown in FIG. 1 is assembled (the flange plate shown in FIG. 4 is used as the flange plate).

According to the kit 10 of the present invention, as shown in FIG. 5, the support plate 1 holding the filter 9 in the filter arrangement portion 12 (preferably, the support plate 1 fixing the filter 9 by the cover plate 2) and the flange plate 3 can be sandwiched and fixed by sliding clips 4a, 4b, with a U-shaped cross section, onto the frame portion 13 of the support plate 1 and the flange 33 of the flange portion 31 of the flange plate 3, and therefore, the support plate 1 works in conjunction with the flange plate 3 to sandwich and fix the filter 9 in the filter arrangement portion 12 without breaking it. Further, the sandwiching and fixing state of the filter 9 can be released by sliding the clip 4a, 4b, and the flange plate 3 can be removed, and therefore, the filter 9 can be detached without breaking it. In this case, when the packing 5 capable of preventing liquid leakage is provided between the window portion 35 of the flange plate 3 and the window portion 11 of the support plate 1 (the window portion 21 of the cover plate 3 when the cover plate 3 is used), the leakage of floating cells is easily prevented during cell filtration. Even if the clips 4a, 4b are spring-energized clips, instead of the clips shown in FIG. 5, the filter 9 can be sandwiched and fixed without breaking it, and the filter 9 can be detached without breaking it. With respect to the flange plate 3, in addition to the embodiment clamped by the clips, as shown in FIG. 5, it may be an embodiment in which the flange plate and the support plate can be fitted or pivotably attached.

Since the flange plate 3 of the kit 10 shown in FIGS. 1 and 5 has the cup portion 32, the solidification step can be carried out by putting a large amount of a liquid-based cell sample containing cells into the cup portion 32. On the other hand, when the solidification step is carried out using a small amount of a liquid-based cell sample, for example, when the liquid-based cell sample is put with a pipette, a flange plate 3 not having the cup portion 32 may be used. In this case, the connecting portion 34 of the flange plate 3 acts in the same manner as that of the cup portion 32. That is to say, the connecting portion 34 prevents the leakage from the side of the liquid-based cell sample, temporarily stores the liquid-based cell sample, and supplies the liquid-based cell sample to the window portion 35 of the flange plate 3 to solidify the cells on the filter.

The flange plate 3 shown in FIG. 1 has the flange portion 31 having the flange 33 and the connecting portion 34, and the cup portion 32, but the flange plate 3 may be composed only of the flange 33. That is to say, the flange plate need not have the connecting portion 34 and the cup portion 32. In this case, if the flange plate 3 has a sufficient thickness to temporarily store the liquid-based cell sample, the window portion 35 prevents the leakage from the side of the liquid-based cell sample, and filters the liquid-based cell sample while temporarily storing the liquid-based cell sample to solidify the cells on the filter.

The kit of the present invention may comprise, as the sandwiching plate, both the cover plate 2 and the flange plate 3, as shown in FIG. 1, or may comprise only one of them. When both the cover plate 2 and the flange plate 3 are simultaneously used, the cover plate 2 mainly acts as the sandwiching plate, and the flange plate 3 supplementarily acts as the same. When either the cover plate 2 or the flange plate 3 is used, any plate acts as the sandwiching plate. When only the flange plate 3 is used as the sandwiching plate, it is preferable that the window portion 35 of the flange portion 31 of the flange plate 3 is provided with a support member capable of supporting the filter, like the cover plate 2.

When only the flange plate 3 is used, like the cover plate 2, if the flange plate 3 has a hollow, into which a tweezer tip can be inserted, adjacent to a position corresponding to the filter arrangement portion 12 of the support plate 1, the filter 9 can be detached without breaking it, even if the filter 9 is attached to the flange plate 3 when the flange plate 3 is removed from the support plate 1. Further, as described above, when the filter arrangement portion 12 has the convex portion, it is preferable that the flange plate 3 has a concave portion at the position corresponding to the convex portion, and the convex portion can be accommodated in the concave portion, like the cover plate 2.

The support plate 1 in the filter holder shown in FIG. 1 has the filter arrangement portion 12 and the frame portion 13; the frame portion has the fitting hollows 15a, 15b for detachably fixing the sandwiching plate (cover plate 2, flange plate 3), the hollows 17, 27 into which a tweezer tip can be inserted in recovery of the filter 9, and the accommodation hollow 18 capable of accommodating the protrusive portion 24 of the sandwiching plate (cover plate 2, flange plate 3); the frame portion can also be used as the portion sandwiched and fixed by the clips 4a, 4b in sandwiching and fixing the flange plate 3; and therefore, it is excellent in sandwiching and fixing properties, detachability, and/or stainability of the filter 9; but the support plate 1 need not have the frame portion. For example, when the sandwiching plate (cover plate 2, flange plate 3) capable of being fitted, clamped, or pivotably-attached to the filter arrangement portion 12 is used; when the filter 9 protrudes from the filter arrangement portion 12; when the sandwiching plate (cover plate 2, flange plate 3) has the cut-out portion as the power point portion; and/or when the flange plate 3 is not used; the support plate 1 need not have the frame portion.

The filter 9 included in the kit of the present invention is not particularly limited, so long as cells can be collected by filtration, and the subsequent staining step, mounting step, and the like can be carried out. For example, an inorganic fiber sheet is preferable, because cells can be fixed in internal voids of the filter, and an operation such as immersion in a reagent is possible. In particular, an inorganic fiber sheet having a porosity of 90% or more is preferable, because not only cells are easily fixed in internal voids of the filter, but also it is excellent in water permeability. As such an inorganic fiber sheet having a porosity of 90% or more, for example, an inorganic fiber nonwoven fabric disclosed in JP 2010-185164 may be used.

As the material of the constituent fibers of the inorganic fiber nonwoven fabric, for example, $SiO_2$, $Al_2O_3$, $B_2O_3$, $TiO_2$, $ZrO_2$, $CeO_2$, $FeO$, $Fe_3O_4$, $Fe_2O_3$, $VO_2$, $V_2O_5$, $SnO_2$, $CdO$, $LiO_2$, $WO_3$, $Nb_2O_5$, $Ta_2O_5$, $In_2O_3$, $GeO_2$, $PbTi_4O_9$, $LiNbO_3$, $BaTiO_3$, $PbZrO_3$, $KTaO_3$, $Li_2B_4O_7$, $NiFe_2O_4$, $SrTiO_3$, or the like may be exemplified. The constituent fibers may be composed of one component of these oxides, or two or more components of these oxides. For example, it may be composed of two components of $SiO_2$—$Al_2O_3$.

The porosity of the inorganic fiber nonwoven fabric is preferably 91% or more, more preferably 92% or more, still more preferably 93% or more, and still more preferably 94% or more. On the other hand, the upper limit of the porosity is not particularly limited, but it is preferably 99.9% or less so as to be excellent in shape stability.

The inorganic fiber nonwoven fabric has a tensile breaking strength of, preferably 0.2 MPa or more, more preferably 0.3 MPa or more, still more preferably 0.4 MPa or more, still more preferably 0.5 MPa or more, and still more preferably 0.55 MPa or more, so that it is not easily damaged by water pressure due to steps such as cell filtration, staining or the like, and it is excellent in handling. The tensile breaking strength is the quotient obtained by dividing the breaking load by the cross sectional area of the inorganic fiber nonwoven fabric. The breaking load is a value obtained by measurement under the following conditions, and the cross sectional area is a value obtained from the product of the width and the thickness of the test piece at the time of measurement.

Product name: Small tensile testing machine
Type: TSM-01-cre manufactured by SEARCH CO., LTD.
Test size: 5 mm in width×40 mm in length
Spacing between chucks: 20 mm
Tensile rate: 20 mm/min.
Initial load: 50 mg/1 d The average fiber diameter of the fibers that constitutes the inorganic fiber nonwoven fabric is not particularly limited, but is preferably 3 µm or less, more preferably 2 µm or less, still more preferably 1 µm or less, and still more preferably 0.8 µm or less, so that it is easy to form holes with a size wherein the fibers can easily hold cells. The lower limit of the average fiber diameter is not particularly limited, it is preferably 0.01 µm or more. The term "average fiber diameter" as used herein means an arithmetic mean value of fiber diameters at 50 points, and the term "fiber diameter" means a fiber thickness measured based on an electron micrograph obtained by photographing the inorganic fiber nonwoven fabric in a visual field covering 10 or more fibers.

The average mass per unit area of the inorganic fiber nonwoven fabric is not particularly limited, but it is preferably 20 g/m$^2$ or less, more preferably 15 g/m$^2$ or less, and still more preferably 10 g/m$^2$ or less, because if the mass per unit area is unnecessarily high, water drainability becomes worse in the cell collection step or staining step, and therefore, it takes time to collect the cells, or it tends to cause uneven staining. The lower limit of the average mass per unit area is not particularly limited, but it is preferably 1 g/m$^2$ or more. The term "average mass per unit area" as used herein means an arithmetic mean value of mass per unit area of 18 samples (inorganic fiber nonwoven fabrics), and the term "mass per unit area" means a value obtained by measuring the area of a surface having the largest area, and the mass, and converting the measured mass into mass per an area of 1 m², based on the measured area and the measured mass.

The average thickness of the inorganic fiber nonwoven fabric is not particularly limited, but it is preferably 400 μm or less, more preferably 300 μm or less, and still more preferably 200 μm or less, because if the average thickness is unnecessarily thick, the volume reduction associated with the drying of a mounting medium increases the possibility that bubbles occur in the observation specimen. The lower limit of the average thickness is not particularly limited, but it is preferably 20 μm or more. The term "average thickness" as used herein means an arithmetic mean value of thicknesses of the sample (inorganic fiber nonwoven fabric) at 54 points, and the term "thickness" means a value obtained by measuring the length between surfaces having a largest area by a micrometer method [load: 0.5 N (measurement area: 14.3 mm in diameter)].

The average pore size of the inorganic fiber nonwoven fabric is not particularly limited, but it is preferably 2 to 40 μm, more preferably 4 to 20 μm, and still more preferably 6 to 10 μm, so that it is easy to hold general cells having a diameter of about 20 μm. The term "average pore size" means an average flow pore diameter value obtained by the method defined in ASTM-F316, and can be measured by, for example, a mean flow point method using a porometer (manufactured by Coulter).

The constituent fibers of the inorganic fiber nonwoven fabric are preferably continuous fibers. This is because if the constituent fibers are short fibers, when the inorganic fiber nonwoven fabric is distorted during the staining step, or when cells retained in the pores of the inorganic fiber nonwoven fabric move, the end portion of the inorganic fiber may damage the cell, but if they are continuous fibers, there is no such fear. The term "continuous fiber" means when an electron micrograph of the inorganic fiber nonwoven fabric is photographed at 5000 times, it is impossible to confirm the end portion of constituent fibers.

It is preferable that the inorganic fiber nonwoven fabric is adhered with an inorganic adhesive. This is because it is excellent in shape stability, it is easy to maintain the pores for holding cells, and it has the effect of preventing the filter from being broken in each step. In particular, it is preferable that the inorganic fiber nonwoven fabric is adhered with an adhesive in an entirety including the inside thereof without forming a film between the fibers, because it is excellent in drainability during a cell collection step or a staining step, the filtration time can be reduced, and staining unevenness can be suppressed.

The inorganic fiber nonwoven fabric, which may be used in the method of the present invention, can be prepared by a known electrostatic spinning method, preferably an electrostatic spinning method combining a sol-gel method and a neutralization spinning method, for example, the method disclosed in JP 2010-185164. The production method disclosed in JP 2010-185164 comprises the steps of:
(1) spinning inorganic gel fibers by an electrospinning method from a spinning inorganic sol solution containing a compound mainly composed of an inorganic component;
(2) forming a gel fiber web by irradiating the inorganic gel fibers with ions having a polarity opposite to that of the inorganic gel fibers to accumulate the inorganic gel fibers;
(3) forming an inorganic fiber web by sintering the gel fiber web;
(4) forming an inorganic fiber web containing an adhering inorganic sol solution by imparting an adhering inorganic sol solution containing a compound mainly composed of an inorganic component to an entirety including the inside of the inorganic fiber web, and removing an excess adhering inorganic sol solution by gas-through; and
(5) forming an inorganic fiber nonwoven fabric adhered with an inorganic adhesive in an entirety including the inside thereof by heating the inorganic fiber web containing an adhering inorganic sol solution.

The shape of the filter 9 of the present invention is not particularly limited, and may be an angular shape such as a square, as shown in FIG. 1, or a round shape such as a circle, as shown in FIG. 6.

The material of members other than the filter included in the kit of the present invention, i.e., the support plate 1, the cover plate 2, the flange plate 3, the clips 4a, 4b, and the packing 5, is not particularly limited, so long as floating cells can be collected, and for example, organic resins (for example, polyamide, polybutylene terephthalate, polycarbonate, polyethylene, polyethylene terephthalate, acrylic, polyacetal, polypropylene, polyphenylene oxide, polyphenylene sulfide, polystyrene, polyvinyl chloride, ABS resin, AS resin, chlorotrifluoroethylene, vinylidene fluoride, perfluoroalkoxy fluorine resin, or the like) may be exemplified. It is preferable that the materials of the members other than the filter are made of organic resins, from the viewpoint of disposability after using the kit.

In the kit of the present invention, as shown in FIG. 5, after assembly, a dispersion of floating cells, which are subjects of an observation specimen, is put into the cup portion 32, and filtration is carried out by gravity, or, if desired, by suction, to collect the cells on the filter 9. The filter 9, on which the cell is collected, for example, while fixing between the support plate 1 and the cover plate 2, may be subjected to a cell fixing step and a staining step using a staining basket and a staining bath, and after staining, the filter 9 is detached from the support plate 1, and moved onto a slide glass, and may be subjected to a mounting step. In this way, if the shape and size when the cell-holding substrate is attached to the cell-holding substrate holder is a rectangle which can be accommodated in a staining basket, it can be accommodated in a staining basket in a state where the cell-holding substrate is attached to the cell-holding substrate holder, and therefore, the cell fixing step and the staining step using a staining basket and a staining bath can be carried out to stain the cells with good workability.

The above explanation is one for, as an embodiment of the cell-holding substrate holder for preparing an observation specimen of the present invention, the filter holder for preparing an observation specimen for floating cells, and for, as an embodiment of the kit for preparing an observation specimen including the same of the present invention, the filter kit (i.e., the case where the cell-holding substrate acts as the filter). The cell-holding substrate holder for preparing an observation specimen of the present invention, and the kit for preparing an observation specimen of the present invention may be used, even when the cell-holding substrate does not act as the filter, for example, even when the cell-holding substrate is a cell culture substrate or a cell adsorbing substrate. For example, a cell solidification step of cells to the cell-holding substrate is carried out, not using the filter holder of the present invention as described above, but using a cell-holding substrate such as a cell culture substrate or a cell adsorbing substrate, and then, it may be subjected to the cell fixing step and the staining step using a staining basket and a staining bath, while sandwiching the cell-holding substrate, in which the cells are held, between the support plate and the sandwiching plate (in particular, the cover plate). In this case, the cell-holding substrate having a thickness suitable for an observation specimen to be observed by a microscope may be used, and for example, a glass substrate, a membrane, an inorganic fiber sheet, or the like, may be used. The cell solidification step of cells to the cell-holding substrate can be carried out by, for example, the step of culturing and adhering adherent cells on a cell culture substrate; the step of placing a porous cell adsorbing substrate, such as an inorganic fiber sheet, which is used as the filter above, on the bottom of a culture vessel, and pouring a cell dispersion and allowing it to stand, and adsorbing cells by spontaneous sedimentation; or the step of electrostatically adsorbing cells, using the charge of the cell surface and a cell adsorbing substrate.

The cell-holding substrate holder for preparing an observation specimen of the present invention, and the kit for preparing an observation specimen of the present invention can be used in the method of preparing an observation specimen of the present invention.

The method of preparing an observation specimen of the present invention (hereinafter sometimes referred to as the method of the present invention) may comprise a cell collection step using an inorganic fiber aggregate, a wet fixation step, a staining step, a clearing step, and a mounting step.

In the cell collection step in the method of the present invention, cells are collected using an inorganic fiber aggregate. The collection method is not particularly limited, so long as cells in a sample can be collected in the inorganic fiber aggregate in an amount sufficient for cytology.

For example, a cell collection plate having a filter portion formed at the central portion of a substrate is prepared by attaching an inorganic fiber aggregate of an appropriate size on at least one surface (preferably one surface) of a substrate having a window at the central portion so as to completely cover the window, and a sample is passed through the filter portion (filtration) to carry out the collection. Alternatively, a cell collection plate having a filter portion formed at the central portion of a substrate is prepared by attaching two substrates having a window at the central portion in the state of sandwiching an inorganic fiber aggregate of an appropriate size between the substrates, and a sample is passed through the filter portion (filtration) to carry out the collection. The size and thickness of the substrate is not particularly limited, but taking into consideration the use of a conventional staining basket, it is preferably a shape and thickness according to a slide glass for preparing an observation specimen.

More particularly, in the case of a liquid-based cell sample, the sample as it is, or a suspension diluted with an appropriate liquid (for example, physiological saline, a cell fixing solution, or the like) is added dropwise to the upper surface of the filter portion composed of an inorganic fiber aggregate, and filtered by gravity, or if desired by suction, to collect the cells. In particular, the filtration method by gravity is preferable, because it is unlikely to damage or degenerate the cells. When the amount of a liquid-based cell sample is large, a sufficient amount of cells can be collected by carrying out the filtration operation of the liquid-based cell sample in a state where a liquid storage means (for example, a cylinder having a through-hollow portion) is disposed on the filter portion. Further, the filtration operation can be carried out after removing excess liquid from the liquid-based cell sample by centrifugation.

When the sample is not a liquid-based cell sample, the collection operation can be carried out after the sample is dispersed in an appropriate liquid (for example, physiological saline, a cell fixing solution, or the like).

The inorganic fiber aggregate used in the method of the present invention is preferably an inorganic fiber sheet capable of collecting cells by filtration and capable of being flat and thin. As such an inorganic fiber sheet, for example, an inorganic fiber nonwoven fabric may be exemplified, and it is preferable, because cells can be held in the internal voids of the filter, and an operation such as immersing in a reagent is possible. In particular, an inorganic fiber nonwoven fabric having a porosity of 90% or more is preferable, because not only cells are easily held in internal voids of the filter, but also it is excellent in water permeability. The above explanation for the inorganic fiber nonwoven fabric, which can be used in the kit of the present invention can be applied to the inorganic fiber nonwoven fabric, which can be used in the method of the present invention.

The wet fixing step in the method of the present invention is a step of immersing the inorganic fiber aggregate, in which cells are collected, in a reagent (a fixing solution, for example, 95% ethanol) to fix the cells, in order not to degenerate the cells collected in the inorganic fiber aggregate. The wet fixing step can be carried out according to the wet fixing operation in the conventional and common method for preparing an observation specimen using a slide glass. In the wet fixing operation in the conventional method for preparing an observation specimen, cells smeared on a slide glass are easy to dry, and therefore, it was requested that wet fixation be carried out within a few seconds, but in the method of the present invention, since the inorganic fiber aggregate has water retentivity, the cells do not dry even if left for a few minutes (for example, 3 minutes to 10 minutes), and stable wet fixing can be carried out.

The staining step in the method of the present invention is a step of staining the cells collected in the inorganic fiber aggregate, after wet fixing is completed, by an appropriately-selectable staining method depending on the purpose of use (inspection purpose). The staining step can be carried out according to the staining operation in the conventional and common method for preparing an observation specimen using a slide glass. In the staining step of the method of the present invention, the use of a staining basket and a staining bath is not essential, but it is preferable to use a staining basket and a staining bath from the viewpoint that a large amount of inorganic fiber aggregates can be treated at once.

As the staining method, which may be used in the staining step in the method of the present invention, for example, Papanicolaou stain, PAS stain, or Alcian blue stain may be exemplified.

The clearing step in the method of the present invention is a step of making cells transparent by dehydrating the cells collected in the inorganic fiber aggregate, after staining is completed, and immersing them in xylene or the like. The clearing step can be carried out according to the clearing operation in the conventional and common method for preparing an observation specimen using a slide glass.

The mounting step in the method of the present invention is a step of sealing the inorganic fiber aggregate holding the stained cells with a mounting medium under a cover glass. In the method of the present invention, a mounting medium having a refractive index equivalent to that of constituent fibers of the inorganic fiber aggregate is used. The term "equivalent" as used herein means that it is within ±0.05 of the refractive index. As the mounting medium which can be used in the method of the present invention, for example, Neo-Mount (registered trademark)(Merck #109016, refractive index: 1.46), Soft Mount (registered trademark) (Wako Pure Chemical Industries #192-16301, refractive index: 1.50), New M•X (Matsunami Glass Industry #FX00100, refractive index: 1.545), MGK-S (Matsunami Glass Industry #FK00100, refractive index: 1.545), Multimount 480 (Matsunami Glass Industry #FM48001, refractive index: 1.49), Multimount 220 (Matsunami Glass Industry #FM 22001, refractive index: 1.49), Marinol (MUTO PURE CHEMICALS CO., LTD. #20091, refractive index: 1.572), or the like, may be used.

The method of preparing an observation specimen of the present invention can be carried out using the cell-holding substrate holder for preparing an observation specimen of the present invention and the kit for preparing an observation specimen of the present invention.

EXAMPLES

The present invention now will be further illustrated by, but is by no means limited to, the following Examples.

In accordance with the conditions as described in the Examples 1 and 2 and Comparative Examples 1 and 2 below, cells were collected or smeared, and then fixed. Subsequently, Papanicolaou stain was carried out using Papanicolaou.Hematoxylin Stain Solution (Wako Pure Chemical Industries #168-18941), Papanicolaou EA 100 Stain Solution (#164-18921), and Papanicolaou OG 100 Stain Solution (#161-18931), and a staining basket and a staining bath in accordance with the instructions in the attached manual. Clearing after staining was also carried out in accordance with the instructions in the manual, using a xylene bath. The cells were mounted with a commercially-available mounting medium (Softmount (registered trademark), Wako Pure Chemical Industries, #192-16301, refractive index: 1.50) to prepare observation specimens.

Example 1

A silica continuous fiber aggregate (average mass per unit area: 7.42 g/m$^2$, average thickness: 142 average pore size: 7 average fiber diameter: 0.73 porosity: 95%, breaking load per mass per unit area: 0.57 MPa, refractive index of fiber material: 1.46), which was prepared by applying a silica sol solution to an entirety including the inside of an inorganic fiber web (which was obtained by a combination of a sol-gel method and a neutralization spinning method) and heating, and which was adhered with a silica adhesive in an entirety including the inside thereof without forming a film, was cut into a rectangle of 30 mm in width and 26 mm in length, and a hole of 20 mm in diameter of an aluminum plate of 76 mm in width and 26 mm in length was covered with the silica continuous fiber aggregate, and adhered with an epoxy resin adhesive to prepare a filter (filter surface: 20 mm in diameter, about 3.1 cm$^2$ in area). Subsequently, a cylinder with a diameter of 20 mm was fixed to the filter with a clip via an O-ring (a packing), so that the filter portion was communicated with the hollow portion of the cylinder.

Subsequently, 10 mL of a physiological saline dispersion (5×10$^4$ cells/mL) of HepG2 cells (a cell line derived from human liver cancer), which was likened to a liquid-based cell sample, was put into the hollow portion of the cylinder, and filtered by gravity. The cells were collected with the filter of the silica continuous fiber aggregate, and immediately immersed in a 95% ethanol bath to fix the cells.

Example 2

The cells were collected with the silica continuous fiber aggregate in a similar fashion to that of Example 1, allowed to stand at room temperature for 3 minutes, and immersed in a 95% ethanol bath to fix the cells.

Comparative Example 1

Physiological saline containing HepG2 cells (5×10$^5$ cells) was centrifuged to remove the supernatant, and the cell pellet was prepared. The cell pellet was smeared by a wedge method on a range of about 9.3 cm$^2$ of a slide glass (MUTO PURE CHEMICALS CO., LTD., #511617), which was subjected to a cell peeling prevention coating treatment. Immediately after smearing, the cells were immersed in a 95% ethanol bath to fix the cells.

Comparative Example 2

The cells were smeared on a slide glass in a similar fashion to that of Comparative Example 1, allowed to stand at room temperature for 3 minutes, and immersed in a 95% ethanol bath to fix the cells.

<<Comparison Results>>

Figure 7:
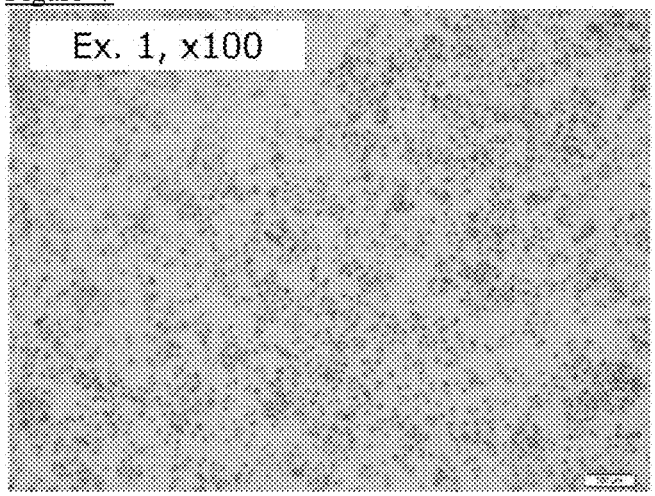
FIG. 7 is a photomicrograph showing a cell image obtained by observing the observation specimen of Example 1 with an optical microscope (magnification: 100 times).
Figure 8:
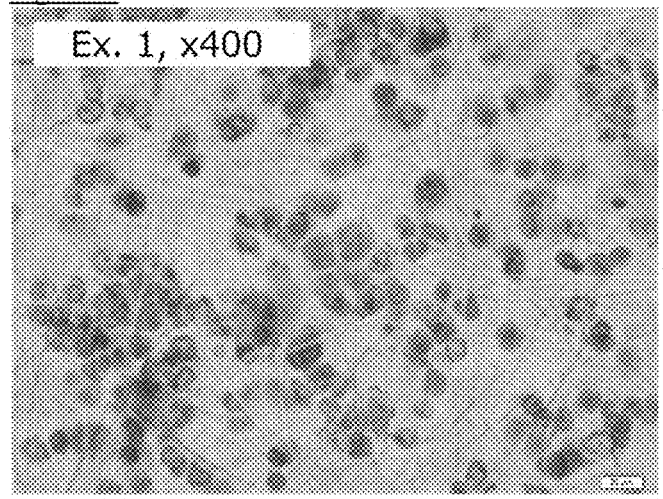
FIG. 8 is a photomicrograph showing a cell image obtained by observing the observation specimen of Example 1 with an optical microscope (magnification: 400 times).

Cell images obtained by observing the observation specimen of Example 1 (fixed immediately after collecting cells) with an optical microscope are shown in FIG. 7 (magnification: 100 times) and FIG. 8 (magnification: 400 times).

Figure 9:
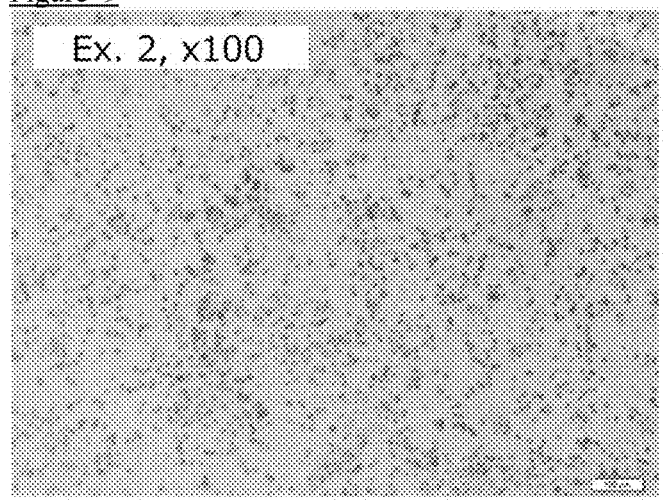
FIG. 9 is a photomicrograph showing a cell image obtained by observing the observation specimen of Example 2 with an optical microscope (magnification: 100 times).
Figure 10:
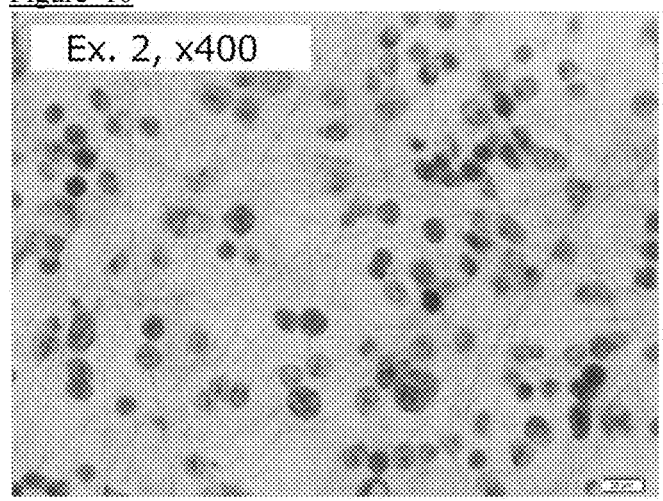
FIG. 10 is a photomicrograph showing a cell image obtained by observing the observation specimen of Example 2 with an optical microscope (magnification: 400 times).

Cell images obtained by observing the observation specimen of Example 2 (fixed after collecting cells and allowing it to stand at room temperature for 3 minutes) with an optical microscope are shown in FIG. 9 (magnification: 100 times) and FIG. 10 (magnification: 400 times).

Figure 11:
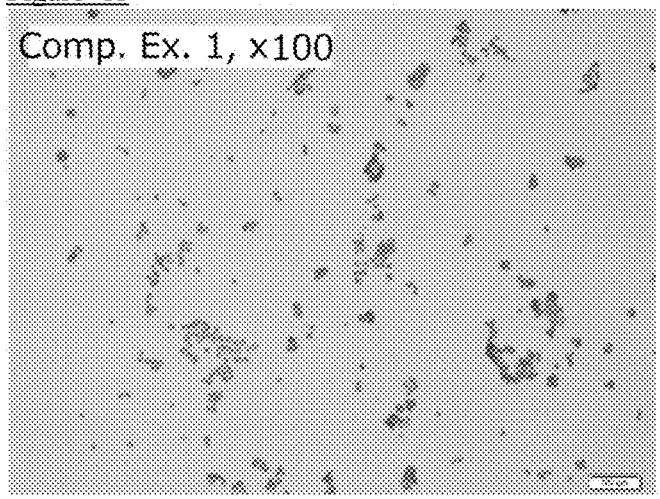
FIG. 11 is a photomicrograph showing a cell image obtained by observing the observation specimen of Comparative Example 1 with an optical microscope (magnification: 100 times).
Figure 12:
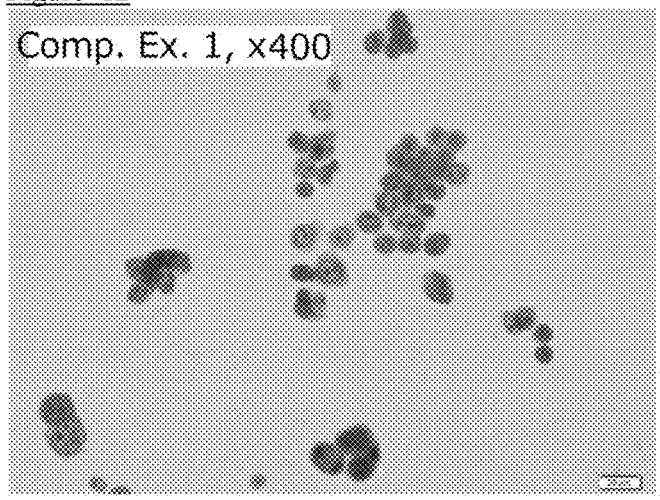
FIG. 12 is a photomicrograph showing a cell image obtained by observing the observation specimen of Comparative Example 1 with an optical microscope (magnification: 400 times).

Cell images obtained by observing the observation specimen of Comparative Example 1 (fixed immediately after smearing cells) with an optical microscope are shown in FIG. 11 (magnification: 100 times) and FIG. 12 (magnification: 400 times).

Figure 13:
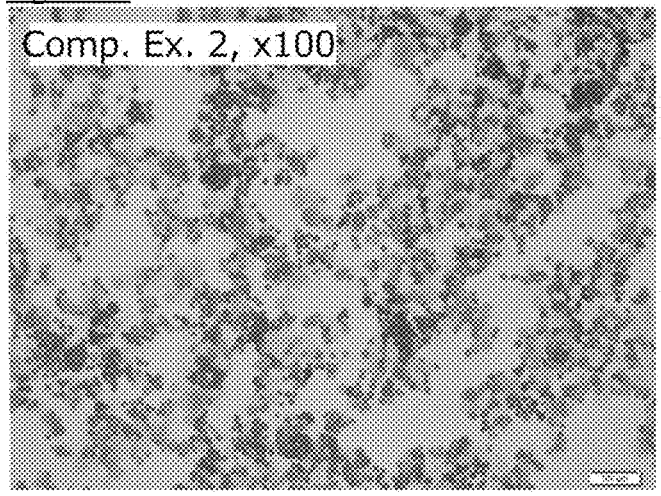
FIG. 13 is a photomicrograph showing a cell image obtained by observing the observation specimen of Comparative Example 2 with an optical microscope (magnification: 100 times).
Figure 14:
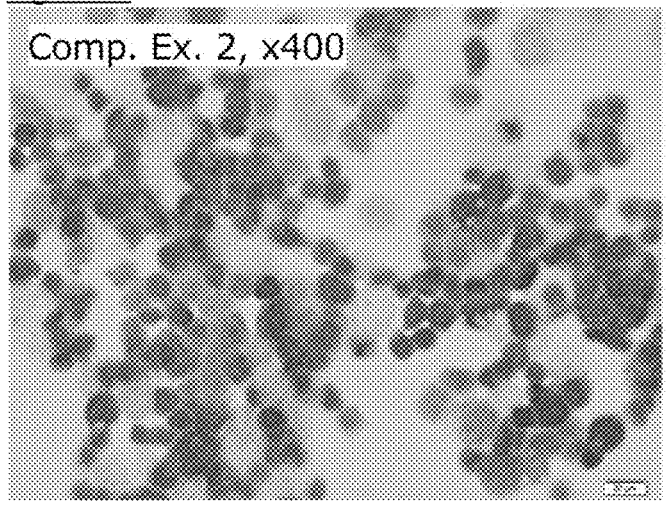
FIG. 14 is a photomicrograph showing a cell image obtained by observing the observation specimen of Comparative Example 2 with an optical microscope (magnification: 400 times).

Cell images obtained by observing the observation specimen of Comparative Example 2 (fixed after smearing cells and allowing it to stand at room temperature for 3 minutes) with an optical microscope are shown in FIG. 13 (magnification: 100 times) and FIG. 14 (magnification: 400 times).

In FIGS. 7 to 14, the cells that appear dark or light gray are actually stained blue. In FIG. 14, the cells that appear dark gray to black are actually stained scarlet to brown, due to the swelling of the cells.

1. Cell Retentivity

The capturing surface (5 places) of the observation specimen of Example 1 and the smeared surface (5 places) of the observation specimen of Comparative Example 1 were randomly photographed at 100-fold observation, using an optical microscope (Olympus Co. Ltd., inverted microscope IX73PI-22FL/PH). In Example 1, at least 1000 or more cells were uniformly observed in all visual fields (FIG. 7). On the other hand, in Comparative Example 1, there were two visual fields where about 500 cells were observed, but there were three visual fields where almost no cells (50 or less cells) were observed and it seemed that cell detachment occurred. FIG. 11 is a photomicrograph in which about 500 cells were observed.

2. Resistance to Drying

In Example 2, even when the cells were allowed to stand at room temperature for 3 minutes, no change in stainability occurred (FIG. 10), but in Comparative Example 2, the swelling of the cells occurred, and stainability changed (FIG. 14).

3. Observability (Intracellular)

In Example 1, an observation image that can sufficiently discriminate cell organelles was obtained even at high magnification (400 times) observation (FIG. 8). On the other hand, in Comparative Example 1, the cells spread a little, and it was easy to observe cell organelles.

4. Observability (Three-Dimensional Properties)

In Example 1, three-dimensional properties of individual cells and three-dimensional positional relationship between cells were maintained (FIG. 8). On the other hand, in Comparative Example 1, all cells spread a little to stick to the slide glass, and therefore, the original three-dimensional structure of the cell disappeared (FIG. 12).

These results are shown in Table 1.

TABLE 1

|  | Examples 1 and 2 | Comparative Examples 1 and 2 |
| --- | --- | --- |
| Cell retentivity | ◎ | X |
| Resistance to drying | ◎ | X |
| Observability (intracellular) | ○ | ◎ |
| Observability (three-dimensional properties) | ◎ | X |

INDUSTRIAL APPLICABILITY

The cell-holding substrate holder for preparing an observation specimen, the cell-holding substrate kit, and the method of preparing an observation specimen of the present invention can be used in pathological diagnosis, such as cytology, and in the field of research using cells, such as medicine, pharmacy, life science, or the like.

Although the present invention has been described with reference to specific embodiments, various changes and modifications obvious to those skilled in the art are possible without departing from the scope of the appended claims.

REFERENCE SIGNS LIST

10 . . . filter kit for preparing an observation specimen for floating cells;
1 . . . support plate; 2 . . . cover plate;
3 . . . flange plate; 4a, 4b . . . clip;
5 . . . packing; 9 . . . filter; 11 . . . window portion;
12 . . . filter arrangement portion; 13 . . . frame portion;
14 . . . support member; 15a, 15b . . . fitting hollow;
16 . . . connecting hole; 17 . . . hollow; 18 . . . accommodation hollow;
19 . . . through-hole (liquid-passage structure);
21 . . . window portion; 22 . . . support member;
23a, 23b . . . fitting claw; 24 . . . protrusive portion; 27 . . . hollow; 29 . . . through-hole (liquid-passage structure);
31 . . . flange portion; 32 . . . cup portion; 33 . . . flange; 34 . . . connecting portion; 35 . . . window portion; 36 . . . connecting protrusion.

The invention claimed is:

1. A cell-holding substrate holder for preparing an observation specimen, said holder comprising:
(1) a support plate having a cell-holding substrate arrangement portion having a window portion through which water can pass; and
(2) a removable sandwiching plate which has a window portion through which water can pass, and is capable of working in conjunction with the support plate to sandwich and fix a cell-holding substrate in the cell-holding substrate arrangement portion,
wherein the support plate has hollows on both sides of the window portion, and the sandwiching plate is a cover plate having claws which can be fitted into both of the hollows.

2. The cell-holding substrate holder for preparing an observation specimen according to claim 1, wherein the support plate has the cell-holding substrate arrangement portion and a frame portion.

3. The cell-holding substrate holder according to claim 2, further comprising a flange plate having a flange portion capable of abutting to the frame portion of the support plate, and a clip capable of sandwiching and fixing the frame portion of the support plate and the flange portion of the flange plate.

4. The cell-holding substrate holder according to claim 3, wherein the flange plate has a cup portion, which a sample can be put into, and can communicate with a window portion of the flange portion.

5. The cell-holding substrate holder according to claim 4, wherein the cup portion can be separated.

6. The cell-holding substrate holder according to claim 1, wherein the window portion of the support plate is provided with a support member capable of supporting the cell-holding substrate.

7. The cell-holding substrate holder according to claim 1, wherein a shape and a size of the support plate is a rectangle which can be accommodated in a staining basket.

8. The cell-holding substrate holder according to claim 1, wherein the support plate and/or the cover plate is provided with a hollow into which a tweezer tip can be inserted.

9. The cell-holding substrate holder according to claim 1, wherein all materials are made of organic resin.

10. The cell-holding substrate holder according to claim 1, wherein the cover plate has a power point portion capable of applying a force.

11. The cell-holding substrate holder according to claim 1, wherein the cell-holding substrate arrangement portion of the support plate and/or the cover plate has a liquid-passage structure.

12. A kit for preparing an observation specimen, comprising the cell-holding substrate holder according to claim 1, and a cell-holding substrate.

13. The kit according to claim 12, wherein the cell-holding substrate is an inorganic fiber sheet having a porosity of 90% or more.

14. The kit according to claim 12, wherein a shape and a size is a rectangle which can be accommodated in a staining basket, when the cell-holding substrate is attached to the cell-holding substrate holder.

15. A method of preparing an observation specimen, comprising:
fixing an inorganic fiber aggregate as a cell-holding substrate to a cell-holding substrate holder for preparing an observation specimen, said holder comprising:
(1) a support plate having a cell-holding substrate arrangement portion having a window portion through which water can pass; and
(2) a removable sandwiching plate which has a window portion through which water can pass, and is capable of working in conjunction with the support plate to sandwich and fix the cell-holding substrate in the cell-holding substrate arrangement portion,
wherein the support plate has hollows on both sides of the window portion, and the sandwiching plate is a cover plate having claws which can be fitted into both of the hollows; and preparing the observation specimen on the cell-holding substrate, including collecting cells with the cell-holding substrate, performing wet fixation of the cells as they are, staining the cells, and encapsulating the cells with an encapsulant having a refractive index equivalent to that of the inorganic fiber.

\* \* \* \* \*